United States Patent
Iftime et al.

(10) Patent No.: US 11,958,747 B2
(45) Date of Patent: Apr. 16, 2024

(54) ANNEALED METAL NANO-PARTICLE DECORATED NANOTUBES

(71) Applicants: Palo Alto Research Center Incorporated, Palo Alto, CA (US); United States of America as Represented by the Administrator of the NASA, Washington, DC (US); Bay Systems Consulting, Inc., Mountain View, CA (US)

(72) Inventors: Gabriel Iftime, Dublin, CA (US); Beomseok Kim, Hayward, CA (US); Clinton J. Smith, San Francisco, CA (US); Eric D. Cocker, Redwood City, CA (US); Junhua Wei, Mountain View, CA (US); David Eric Schwartz, Concord, MA (US); Meyya Meyyappan, Pacifica, CA (US); Rahul Pandey, San Jose, CA (US); Yong Zhang, Millbrae, CA (US)

(73) Assignees: SRI INTERNATIONAL, Menlo Park, CA (US); UNITED STATES OF AMERICA AS REPRESENTED BY THE ADMINISTRATOR OF THE NASA, Washington, DC (US); BAY SYSTEMS CONSULTING, INC., Mountain View, CA (US)

( * ) Notice: Subject to any disclaimer, the term of this patent is extended or adjusted under 35 U.S.C. 154(b) by 0 days.

(21) Appl. No.: 17/235,825

(22) Filed: Apr. 20, 2021

(65) Prior Publication Data
US 2021/0253429 A1 Aug. 19, 2021

Related U.S. Application Data

(63) Continuation of application No. 15/853,432, filed on Dec. 22, 2017, now Pat. No. 11,072,531.

(51) Int. Cl.
*C01B 32/168* (2017.01)
*C01B 32/176* (2017.01)
(Continued)

(52) U.S. Cl.
CPC .......... *C01B 32/168* (2017.08); *C01B 32/176* (2017.08); *G01N 27/12* (2013.01); *G01N 33/0036* (2013.01)

(58) Field of Classification Search
CPC ... C01B 32/168; C01B 32/176; C01B 32/158; C01B 32/159; C01B 32/16;
(Continued)

(56) References Cited

PUBLICATIONS

Liu, et al., Fabrication of platinum-decorated single-walled carbon nanotube based hydrogen sensors by aerosol jet printing, Nanotechnology 2012; 23: 505301, pp. 1-7 (Year: 2012).*
(Continued)

*Primary Examiner* — Daniel C. McCracken
(74) *Attorney, Agent, or Firm* — Shun Yao; Yao Legal Services, Inc.

(57) ABSTRACT

Disclosed are methods and systems of providing carbon nanotubes decorated with polymer coated metal nanoparticles. Then, annealing the metal coated carbon nanotubes to reduce a quantity of hydrophilic components of the polymer coating.

20 Claims, 8 Drawing Sheets

(51) Int. Cl.
*G01N 27/12* (2006.01)
*G01N 33/00* (2006.01)

(58) Field of Classification Search
CPC ... C01B 32/162; C01B 32/164; C01B 32/166; C01B 32/17; C01B 32/172; C01B 32/174; C01B 32/178; C01B 2202/00; C01B 2202/02; C01B 2202/04; C01B 2202/06; C01B 2202/08; C01B 2202/10; C01B 2202/20; C01B 2202/22; C01B 2202/24; C01B 2202/26; C01B 2202/28; C01B 2202/30; C01B 2202/32; C01B 2202/34; C01B 2202/36; G01N 27/12; G01N 33/0036; D01F 9/12; D01F 9/127; D01F 9/1271; D01F 9/1272; D01F 9/1273; D01F 9/1274; D01F 9/1275; D01F 9/1276; D01F 9/1277; D01F 9/1278; D01F 9/133
See application file for complete search history.

(56) References Cited

PUBLICATIONS

Hussain, et al., Heat-treatment effects on the ORR activity of Pt nanoparticles depsotied on multi-walled carbon nanotubes using magnetron sputtering technique, International Journal of Hydrogen Energy 2017; 42: 5958-5970 (Year: 2017).*

Selvaraj, et al., Electrocatalytic oxidation of formic acid and formaldehyde on nanoparticle decorated single walled carbon nanotubes, Journal of Colloid and Interface Science 2009; 333: 254-262 (Year: 2009).*

Kharisov, et al., Decoration of Carbon Nanotubes With Metal Nanoparticles: Recent Trends, Synthesis and Reactivity in Inorganic, Metal-Organic, and Nano-Metal Chemistry 2016; 46: 55-76. (Year: 2016).*

Definition of "predefined," accessed online at https://www.merriam-webster.com/dictionary/predefined on May 3, 2023 (Year: 2023).*

Definition of "threshold," accessed online at https://www.merriam-webster.com/dictionary/threshold on May 3, 2023 (Year: 2023).*

* cited by examiner

ANNEALED METAL NANO-PARTICLE DECORATED NANOTUBES

RELATED APPLICATIONS

This application is a continuation of U.S. patent application Ser. No. 15/853,432, U.S. Pub. No. US20190194019A1, titled "Annealed Metal Nano-Particle Decorated Nanotubes," by inventors Gabriel Iftime, Beomseok Kim, Clinton Smith, Eric Cocker, Junhua Wei, David Eric Schwartz, Meyya Meyyappan, Rahul Pandey, and Yong Zhang, filed 22 Dec. 2017.

STATEMENT REGARDING FEDERALLY SPONSORED RESEARCH AND DEVELOPMENT

This invention was made with government support under Contract No. DE-AR0000542 MONITOR-SPHINCS awarded by the Advanced Research Projects Agency-Energy. The Government has certain rights in this invention.

TECHNICAL FIELD

Implementations of the present disclosure relate to nanoparticle based materials for gas sensors.

BACKGROUND

Various techniques may be utilized for gas leak detection, with each approach having advantages trade-offs. Such techniques include, for example, catalytic bead sensors, metal-oxide-semiconductor (MOS) sensors, non-dispersive infrared sensors, and infrared laser-based sensors. Some techniques may be compact and integrated into printed circuit boards. Depending on materials and techniques used, various methodologies may provide different size, power level, expense, or other tradeoffs.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

Natural gas leaks even in low levels, contribute greatly to global warming. For Example, methane leaks in an industrial setting may accumulate in the atmosphere and produce greenhouse effects. In addition, natural gas or methane leaks may also produce hazardous environments that may be flammable or produce potential health consequences to persons exposed to such environments. Some techniques for measuring natural gas or methane leaks including catalytic bead sensors, MOS sensors, non-dispersive infrared, and infrared laser-based approaches may be limited in detection limit, size, power consumption, expense, or other limitations.

Compact devices with low power consumption may provide improved sensor characteristics for monitoring and reacting to natural gas or methane leaks. However, some compact and low power gas sensors may have reduced detection capability in the presence of certain gases. For example, certain sensors for detecting natural gas or methane may not function properly in the presence of water vapor. Due to the ubiquitous nature of water vapor in normal atmospheric conditions where gas sensors may be helpful, these sensors may have limited lifespans before saturation of the sensors with water vapor. The impact of water vapor on such sensors may reduce the reliability of the devices.

Described herein are embodiments of metal nanoparticle-decorated nanotubes, methods for producing the same, and sensors incorporating the same. Certain embodiments relate to a gas sensor that uses a composition comprising carbon nanotubes (e.g., single-walled carbon nanotubes, or "SWCNTs") decorated with metal nanoparticles as a sensing material. The metal nanoparticles may be coated with a polymer to attach them to the SWCNTs and reduce adsorption of water vapor by the metal nanoparticles. The decorated SWCNTs may then be annealed at a high temperature to carbonize the polymer coating as well as removing oxygen containing functional groups from polymer coating and the SWCNTs. The sensing material may be placed in between interdigitated electrodes of a sensor. When methane gas adsorbs to the sensing material, its electronic state is changed resulting in a change in resistivity that is proportional to the amount of methane adsorbed. This change in resistivity can be measured via a number of resistivity measurement techniques (e.g., voltammetry).

In some embodiments, a process for fabrication of the SWCNT/NP materials includes an annealing step to remove oxygenated functional groups as well as minimize the presence of a polymer coating of the metal nanoparticles. The annealing step may be performed at temperatures of about 350° C. To aid in removal of polymer material and functional groups, the annealing process may be performed in vacuum or in an inert environment such as nitrogen or argon gas. After annealing, the interface between the SWCNT and the metal nanoparticles may include a carbonized or deoxygenated organic material.

In some embodiments, Platinum (Pt) or Palladium (Pd) nanoparticles are used due to their sensitivity to hydrocarbons including alkane gases such as methane, ethane and propane. When the nanoparticles are attached to a conductive or semiconductive material such as a single-walled carbon nanotube (SWCNT) conductivity changes associated with hydrocarbon gas adsorption are measureable. For practical applications, it is important that the sensing materials be relatively insensitive to humidity. Even in conventionally dry conditions, ambient concentrations of water vapor are typically two to three orders of magnitude higher than the concentrations of hydrocarbon gases being monitored. For example, the concentration of a hydrocarbon gas may be on the order of 1 ppm or lower while water vapor concentrations are significantly higher.

In some embodiments, platinum-decorated SWCNT (Pt/SWCNT) materials are synthesized by combining Pt particles and SWCNTs. The Pt nanoparticles may be synthesized by the so called polyol method that includes reduction of Pt salts in the presence of a polyol such as ethylene glycol. During this process, Pt ions are reduced to Pt metal atoms which form nanocrystals that are stabilized by a polymer that has good miscibility in ethylene glycol. For example, in some implementations, polyvinylpyrrolidone (PVP) may be used as a stabilizing polymer for the metal nanoparticles. Other examples of suitable polymers for stabilization of the Pt particles include polyethylene glycol (PEG), poly vinyl alcohol (PVA), poly methacrylic acid, dodecanethiol or other substituted analogues. The addition of the polymer may provide a template to obtain evenly distributed nanoparticles.

In alternate embodiments, platinum-decorated SWCNT (Pt/SWCNT) materials are synthesized by formation of polymer coated platinum nanoparticles directly onto the surface of the carbon nanotubes from metal salts precursors. In this embodiment, the Pt nanoparticles are still synthesized by reduction of Pt salts in ethylene glycol and a dispersant such as PVP, but in the presence of carbon nanotubes dispersed in the reaction mixture. The Pt nanoparticles growth is directly initiated onto the surface of the carbon nanotubes.

The carbon nanotubes may be unfunctionalized so that they may be substantially free of —COOH or —OH groups, or may have a degree of carboxylic acid (—COOH) or hydroxyl (—OH) functionalization. In some embodiments, a lower degree of functionalization or no functionalization may be beneficial for the sensor performance because it keeps undisturbed the electronic structure of the carbon nanotubes. In other embodiments, a higher degree of —COOH an —OH functionalization may be also beneficial because the carboxyl functional groups are negatively charged and can donate their electrons, thus serving as a binding moiety towards Pt nanoparticles, increasing the surface coverage of the SWCNTs by the metal nanoparticles. In addition, the —COOH and —OH groups onto the surface of oxidized SWCNT may enable the SWCNT to be dispersed in an aqueous solvent and ethylene glycol, which is highly desirable for fabrication of well dispersed Pt/SWCNT inks for sensor printing. The optimal degree of functionalization may depend on multiple factors: the type of nanoparticle metal, the type of particle coating polymer and the gas to be sensed. The weight % of —COOH and —OH onto carbon nanotubes is measured by the weight loss in thermogravimetric analysis (TGA) at temperatures below 300° C. when the experiment is run in UHP grade inert gas. In some embodiments, the —COOH and —OH functional groups are being created by extensively oxidizing SWCNT with nitric acid reflux before combining with the metal nanoparticles. A suitable weight % of —COOH and —OH oxygen containing groups ranges from zero (substantially free of functional groups) to up to about 20%. In some embodiments, the range may be about 0.1% to about 5%, about 1% to about 5%, about 4% to about 6%, or another range.

After generating the Pt/SWCNT material as described above, it may be annealed by heating it at a high temperature. For example, the material may be heated at 350° C. for a half hour. In various implementations, the heating may be performed at temperatures between about 350° C. and about 500° C. Furthermore, the annealing process may be performed for about half an hour, an hour, up to four hours, or at another length of time. In some implementations, annealing may be performed in stages at different temperatures and for different lengths of time. The annealing temperature should be high enough to carbonize the polymer material while low enough to prevent the material from catching fire or degrading due to high temperatures. In some implementations, the annealing process may be performed under vacuum conditions or in the presence of an inert gas to remove the hydrophilic oxygen containing groups from the Pt/SWCNT.

While described generally with reference to Pt nanoparticles, in various implementations, the processes for synthesizing the Pt/SWCNT may be performed similarly for other metal nanoparticles. For example, Pd nanoparticles may be used and synthesized into Pd/SWCNT using similar procedures. Additional metal nanoparticles may be used for natural gas sensing or for sensing of other gases. For example, in some embodiments, gold nanoparticles may be used for sensing of hydrogen sulfide. Other metal nanoparticles may be used so long as their size doesn't cause them to burn during annealing processes or otherwise degrade during one of the processing steps. In other embodiments, one or more of palladium, iridium, rhodium, platinum, copper, nickel, chromium, ruthenium, silver or gold may also be used. In other embodiments, the metal decorating nanoparticles consist of an alloy or a mixture of two or more metals.

During synthesis of the metal nanoparticles, PVP, or another polymer, may be used in large concentrations to encapsulate and stabilize the Pt nanoparticles. For example, in some implementations, the weight-to-weight (w/w) ratio by raw materials may be 10 mg SWCNT:50 mg H2PtCl6.6H2O:250 mg PVP. However, as PVP may interfere with the sensor response as the PVP residue functions as a nonconductive material and diffusion barrier some of the polymer material may be removed during processing.

There are several choices of base SWCNT materials to use in the synthesis. SWCNTs with no functional groups are advantaged as they are largely insensitive towards humidity. However, they are difficult to disperse and do not bind well with the metal nanoparticles. As mentioned, SWCNT with carboxyl functional groups (SWCNT-COOH) binds well and is easily dispersed in solvent. Nevertheless, SWCNT-COOH has the disadvantage of being very sensitive to humidity. Therefore, after the Pt is bound with the SWCNT surface, removal of carboxylated functional group is important for enabling the sensors to function in real-world conditions. We achieve this with heat treatment to induce thermal degradation of PVP. In addition, the carboxyl groups of SWCNT-COOH are gradually degraded between 100 and 250° C. This can be seen as a 20% weight decrease up to 350° C. Degradation of the carboxylic acid groups may be the result of the decarboxylation of SWCNT-COOH.

Annealing of the Pt/SWCNT wherein the Pt particles are coated with PVP and the SWCNTs are functionalized with —COOH groups, may result in loss of PVP and —COOH groups. This may provide additional benefits compared to non-annealed Pt/SWCNT. First, the annealed Pt/SWCNT may provide enhanced sensitivity because of lower polymer content and more direct contact between the Pt particles and the SWCNT surface. Second, the annealed Pt/SWCNT may provide reduced water sensitivity because of removal of the hydrophilic carboxyl and other oxygen containing functional groups. This renders the annealed Pt/SWCNT particles more hydrophobic when compared with the Pt/SWCNT particles that are not annealed.

In some implementations, a process for Pt/SWCNT synthesis begins with combining about 1 mL of SWCNT-COOH solution (10 mg/mL $H_2O$) with about 10 mL of Pt nanoparticles solution (65 mM). The combination may be mixed for about 2 min. The solution may then be probe-sonicated for 5 min at 30 W power. After mixing, the combination may be bath-sonicated for 1 hour. The bath sonicated solution may then be placed in a convection oven and EG was evaporated at about 200° C. After the solvent (e.g., ethylene glycol) has evaporated, the solution may be moved into vacuum furnace and heated to 350° C. for 30 min. To produce the sensors, the combined nanoparticle and nanotube residue may be diluted with about 2 mL of DMF and bath-sonicated briefly (<5 sec). The processes described may produce highly hydrophobic composite nanoparticles.

In some implementations, the contact angle measurement of the combined nanoparticles coated on glass slides shows significant change of the hydrophilic behavior between metal nanoparticle coated nanotubes before and after annealing. Coated Pt/SWCNT slides may have a low contact angle for water (e.g., about 34 degrees), which demonstrates hydrophilic characteristics. After annealing, SWCNT-NP may have a much higher contact angle (e.g., about 83 degrees) which demonstrates a improved hydrophobic characteristic when compared with the materials before annealing.

A sensing device as described herein may include a CNT/nanoparticle material deposited on interdigitated metal electrodes. In some embodiments, the electrodes consist of gold vacuum-deposited to about 200 nm thick on a flexible polyethylene napthalate substrate. In other embodiments, the electrodes are formed by printed silver nanoparticle inks. Other substrates and deposition methods may also be used to generate a sensor as described herein. Etched or milled copper, such as on commercial printed circuit boards (PCBs) can also be used. In some implementations, a fixed volume of ink containing SWCNT/NPs is printed on the channels of the sensing device. In some embodiments, the volume of the ink dots (typically, 0.1-0.25 µL) and temperature of the heated surface (typically, 90° C.-110° C.) is determined by the resistance required for the sensing device for optimal performance.

Figure 1:
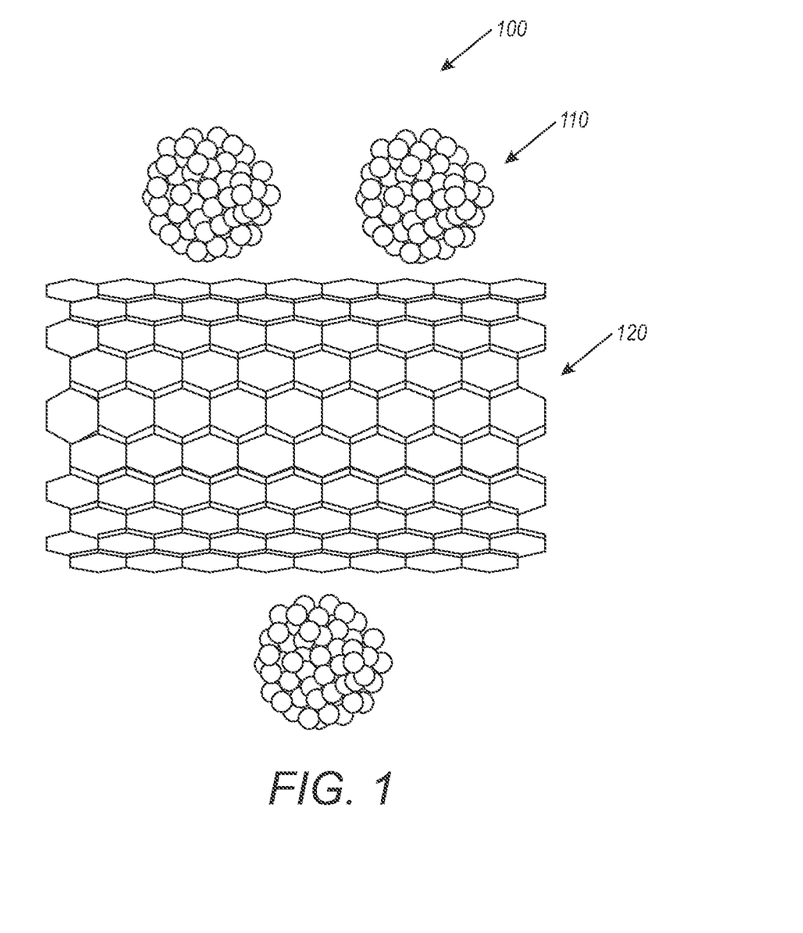
FIG. 1 is a diagram of an example nanoparticle based gas sensing material, according to some aspects of the disclosure.

FIG. 1 is a diagram of an example Pt/SWCNT sensing material 100. The sensing material 100 may include a carbon nanotube 120 with attached Pt nanoparticles 110. As shown the Pt nanoparticles 110 are attached directly to the carbon nanotube 120. This may provide a connection with no hydrophilic properties that has Pt nanoparticles 110 for detecting the presence of natural gas. For example, the close connection between the Pt nanoparticles 110 and the carbon nanotubes 120 may provide an accurate indication of the concentration of natural gas such as methane due to change in resistance of the combined Pt/SWCNT material 100. However, the combination of the Pt nanoparticles 110 and the carbon nanotubes 120 may not be realized without additional binders to combine the materials.

Figure 2A:
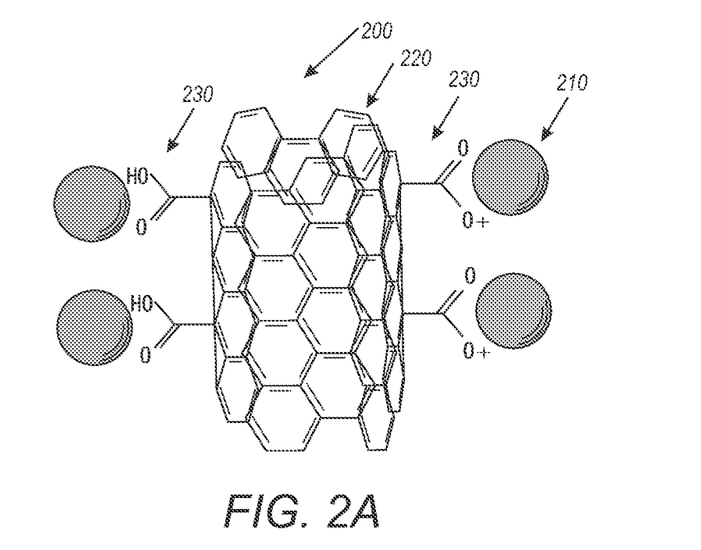
FIG. 2A is a diagram of an example nanoparticle based gas sensing material, according to some aspects of the disclosure.

FIG. 2A is a diagram of an example Pt/SWCNT sensing material 200 that uses a carbon nanotube 220 with carboxyl functional groups (—COOH) 230 combined with polymer coated metal nanoparticles 210. Carbon nanotube 220 represents a carbon nanotube with functionalization with —COOH or other hydrophilic functional groups. The carboxyl functional may be present along the surface of the carbon nanotubes 220, as well as at the ends of the carbon nanotubes. As shown in FIG. 2A, the carboxyl functional groups 230 may aid in distribution and attachment of polymer coated nanoparticles 210 with carbon nanotubes 220. Accordingly, rather than a carbon nanotube 220 without carboxyl functional groups 230, polymer coated nanoparticles 210 may be combined with a carbon nanotube 220 having carboxyl functional groups 230 to improve distribution and attraction of polymer coated nanoparticles 210 with the carbon nanotube 220.

Figure 2B:
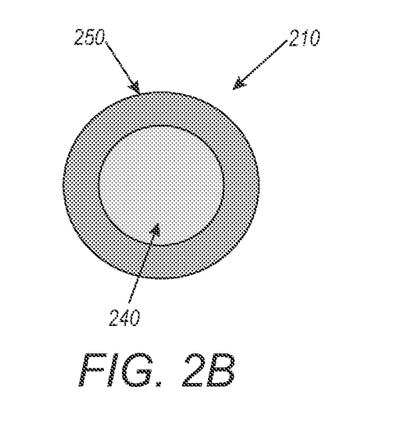
FIG. 2B is a diagram of an example nanoparticle based gas sensing material, according to some aspects of the disclosure.

FIG. 2b is a diagram showing a configuration of a polymer coated nanoparticle 210 including a Pt nanoparticle 240 coated with a polymer coating 250. As described, the polymer coating 250 may comprise PVP or another polymer coating to improve dispersion of the nanoparticles and attachment of the nanoparticles to nanotubes 220. The polymer coating 250 may additionally reduce the hydrophilic properties of the polymer coated nanoparticle 210 compared to a non-coated nanoparticle such that it enables adsorption of natural gas and limits adsorption of water vapor.

Figure 3:
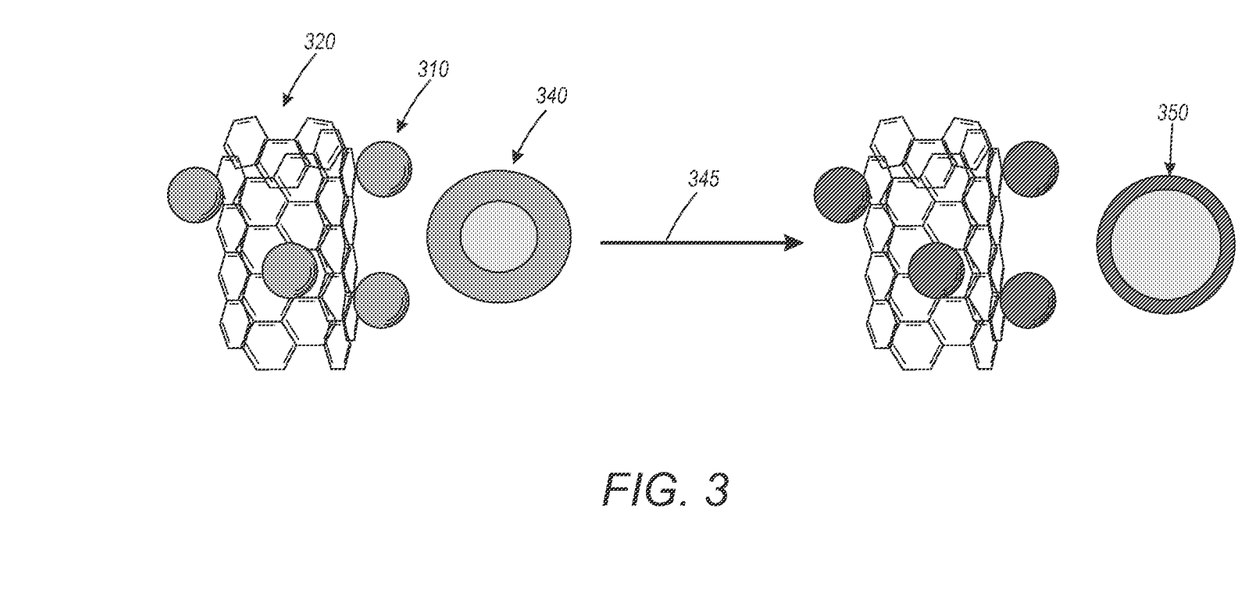
FIG. 3 is a diagram showing annealing processes of an example nanoparticle based sensing material, according to some aspects of the disclosure.

FIG. 3 is a diagram showing changes of a polymer coating 330 to a polymer coating 350 during an annealing process 345. As described above, a metal nanoparticle 310 attached to carbon nanotube 320 is deposited and coated. The metal nanoparticle 310 may be distributed through the carbon nanotubes 320 based on the polymer coating 340. As shown in FIG. 3, Pt nanoparticles are heat treated in an annealing process to remove hydrophilic functional groups. Furthermore, certain portions of polymer coating 340 may be removed to generate a carbonized coating 350 as shown in FIG. 3.

Figure 4:
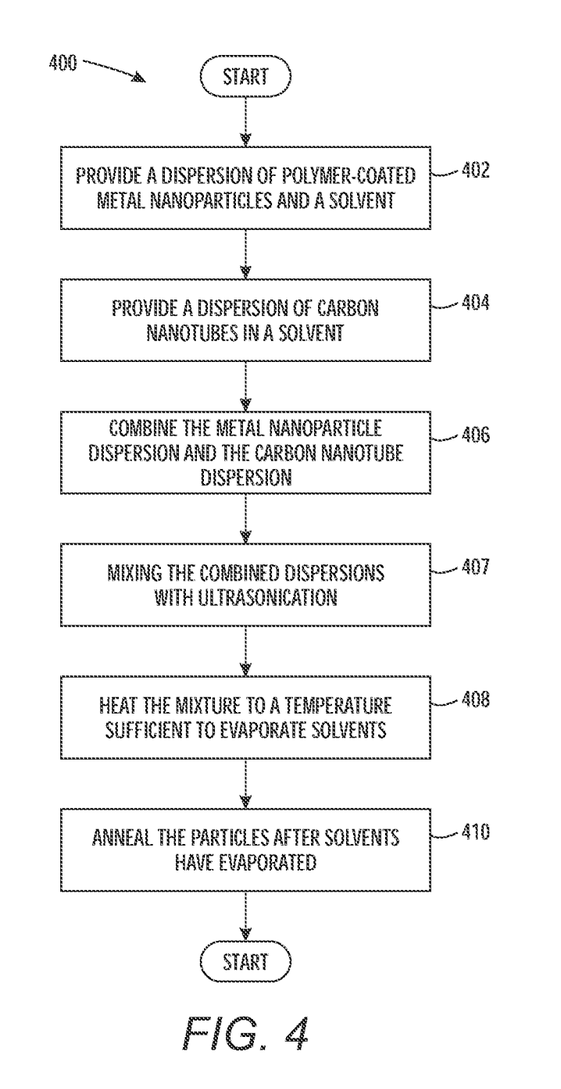
FIG. 4 is a flow diagram depicting an example method of fabricating a nanoparticle based sensing material, according to some aspects of the disclosure.

FIG. 4 is a flow diagram illustrating a method 400 for producing metal nanoparticle-decorated nanotubes in accordance with embodiments of the present disclosure, by mixing polymer coated metal nanoparticles with carbon nanotubes. The method 400 begins at block 402, where a first solution comprising polymer-coated metal nanoparticles is provided. The polymer-coated metal nanoparticles may have structures represented by the polymer-coated metal nanoparticle 210 described with respect to FIGS. 1-3 above. The polymer-coated metal nanoparticles may be synthesized as described herein, or using any adaptations or other suitable synthesis methods. In some embodiments, each polymer-coated metal nanoparticle comprises a Pt or Pd core and a polymer layer comprising PVP. In some embodiments, the polymer-coated metal nanoparticles are dispersed in an organic solvent.

At block 404, a second solution comprising carbon nanotubes is provided. The carbon nanotubes may have functional groups including carboxylic acid (—COOH) and/or hydroxyl (—OH) groups to improve attachment of metal nanoparticles to the carbon nanotubes. The carbon nanotubes may be synthesized as described herein, or using any other adaptations or other suitable synthesis methods. In some embodiments, the carbon nanotubes are SWCNTs. In some embodiments, the carbon nanotubes may be dispersed in an aqueous solvent prior to combination with the metal nanoparticles.

At block 406, a reaction mixture is formed by combining the first solution with the second solution. The combined mixture causes the metal nanoparticles to deposit on the carbon nanotubes.

At block 407, the reaction mixture may be ultrasonicated. For example, the mixture may be ultrasonicated at high power for about 5 minutes or at low power for about an hour. In some embodiments, the mixture may be ultrasonicated at high power for 5 minutes and low power for an hour. These processes might remove PVP from Pt nanoparticles temporarily, expose the Pt nanoparticle surface to SWNT, and enhance binding between SWCNT-COOH and Pt nanoparticles.

At block 408, the reaction mixture is heated to a temperature greater than a glass transition temperature of the polymer of the polymer-coated metal nanoparticles such as 200° C. (a glass transition temperature for PVP, for example, may vary from 100° C. to 180° C. depending on its molecular weight). This process also helps bindings of the nanoparticles towards the SWNT surface. PVP residue might stay in EG or as outer shell of Pt/SWNT. In some embodiments, the nanoparticle-coated metal nanoparticles are treated with a solvent to remove solvent-accessible PVP from surfaces of the nanoparticles.

At block 410, the dry PVP coated metal nanoparticle decorated carbon nanotubes are annealed. The annealing temperature may be at or around about 350° C. In some implementations the annealing temperature may be higher or lower than described herein. The annealing process may further be carried out for about half an hour. In some implementations, the annealing process may be performed for a longer or shorter amount of time. In some embodiments, the resulting carbon nanotubes have a set of attached metal nanoparticles with reduced polymer layers.

Figure 5:
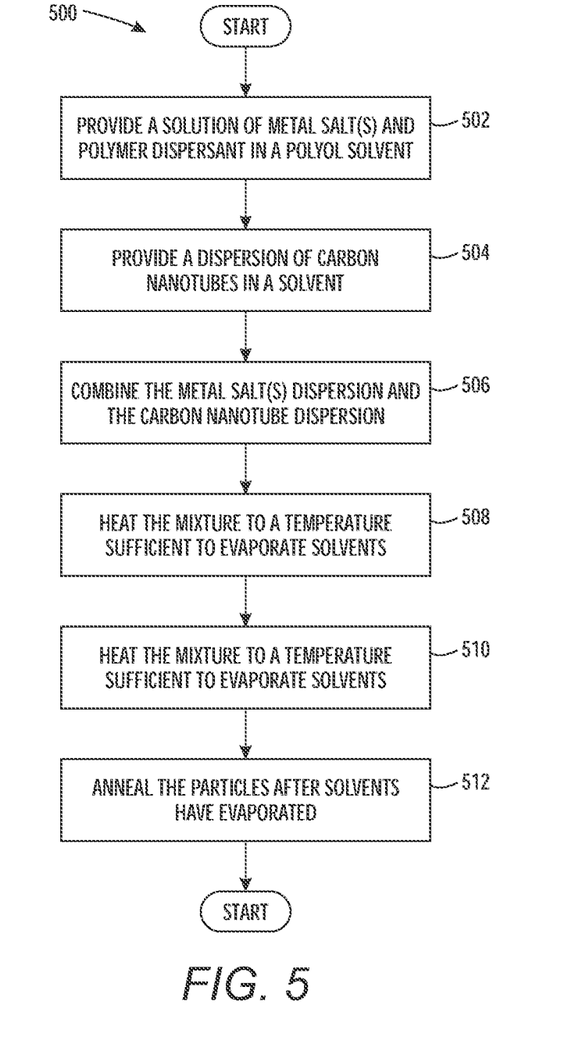
FIG. 5 is a flow diagram depicting an example method of fabricating a nanoparticle based sensing material, according to some aspects of the disclosure.

FIG. 5 is a flow diagram illustrating a method 500 for producing metal nanoparticle-decorated nanotubes in accordance with embodiments of the present disclosure, by direct formation of polymer coated metal nanoparticles onto the surface of the carbon nanotubes from metal salts precursors. The method 500 begins at block 502 where a first solution comprising metal salts and a polymer dispersant in a solvent is provided. At block 504 a solution comprising carbon nanotubes dispersed in a solvent is provided. At block 506 a reaction mixture is formed by combining the first solution with the second dispersion. At block 508 the mixture is heated at a temperature to enable reduction of the metal salts to metal atoms by a polyol such as ethylene glycol. For example, the mixture may be heated to a temperature of greater than 150° C. in the case ethylene glycol is used. In some embodiments, the reaction takes place in a vessel armed with a condenser to enable polyol solvent reflux.

At block 510 the condenser may be removed and the mixture is heated at a temperature that is sufficient to remove the solvents. For example ethylene glycol which boils at 197° C. can easily be removed buy heating at a temperature of about 200° C. as described with reference to block 408 above.

Finally, at block 512 the dry particles obtained after solvent evaporation in block 510 may be annealed at a higher temperature. The annealing temperature may be at or around about 350° C. In some implementations the annealing temperature may be higher or lower than described herein. The annealing process may further be carried out for about half an hour. In some implementations, the annealing process may be performed for a longer or shorter amount of time. In some implementations, the annealing process may be performed for a length of time until the solvents used to combine the metal nanoparticles and carbon nanotubes is evaporated. In some embodiments, the resulting carbon nanotubes have a set of attached metal nanoparticles with reduced polymer layers.

Figure 6A:
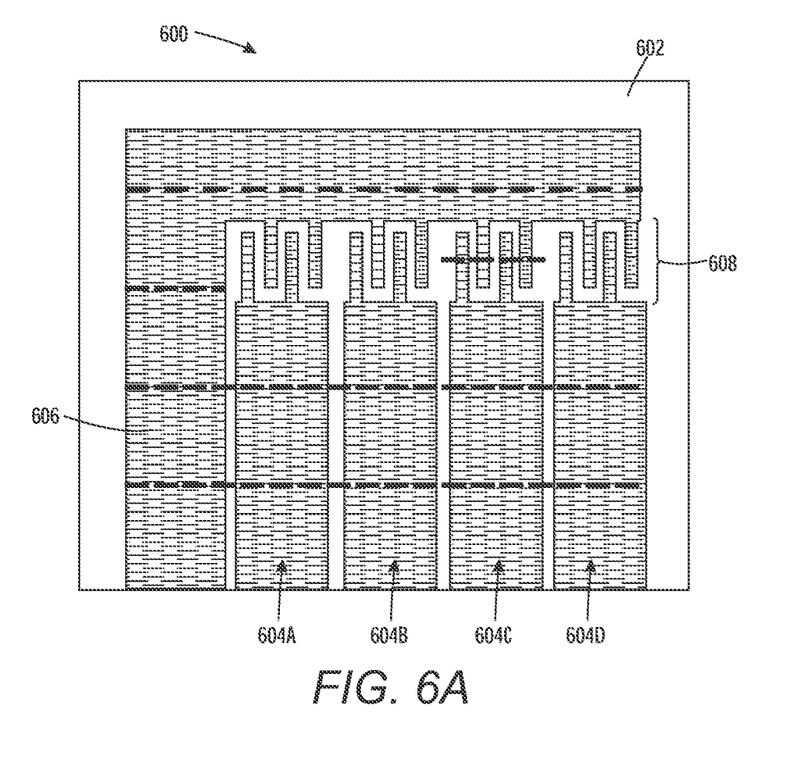
FIG. 6A is a diagram of an example gas sensor using a nanoparticle material, according to some aspects of the disclosure.
Figure 6B:
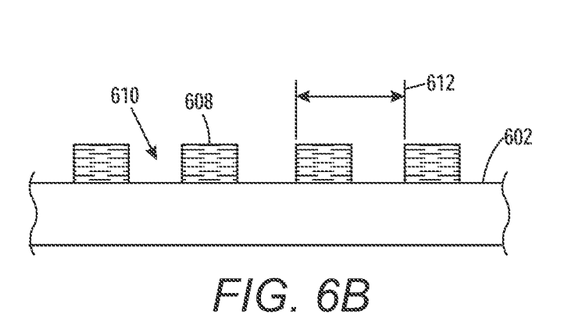
FIG. 6B is a diagram of an example gas sensor using a nanoparticle material, according to some aspects of the disclosure.
Figure 6C:
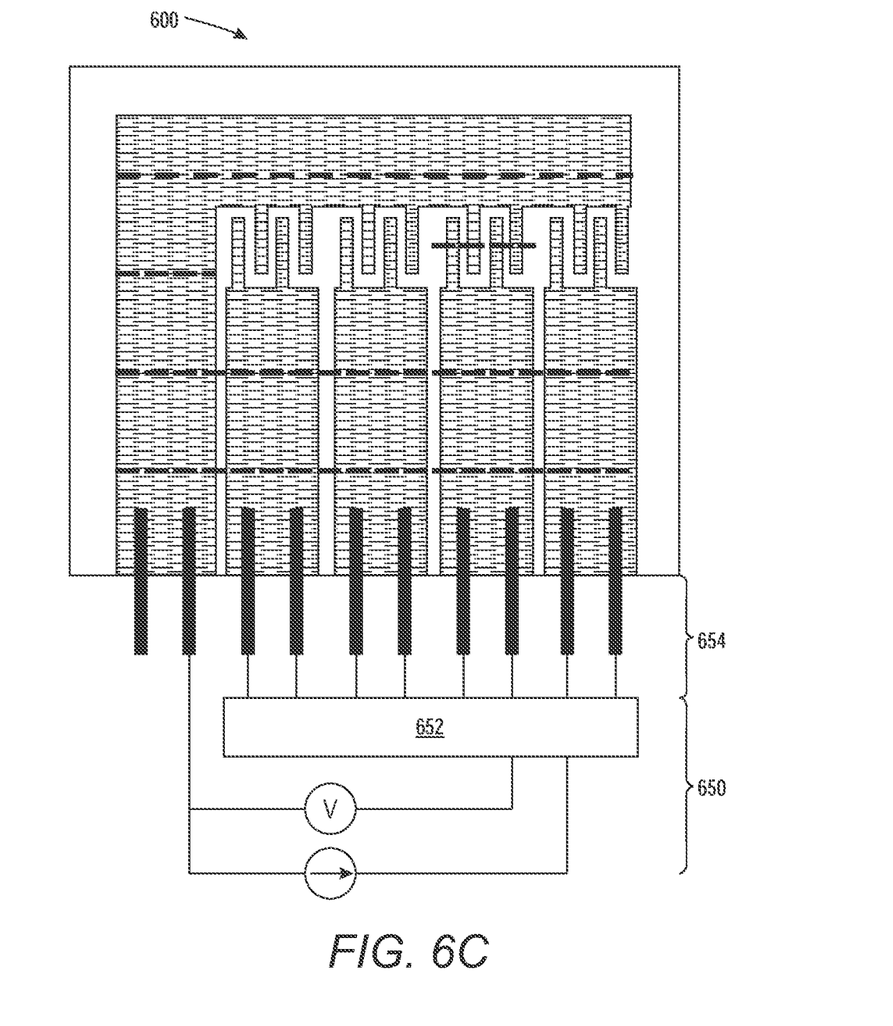
FIG. 6C is a diagram of an example gas sensor using a nanoparticle material, according to some aspects of the disclosure.

FIGS. 6A-6C are diagrams depicting top down and cross-sectional views, respectively, of an exemplary sensor chip 600 according to an embodiment of the present disclosure. The sensor chip 600 includes a substrate 602 having sensors 604A-604D formed on the surface of a semiconductor substrate. Although four sensors are depicted, fewer or additional sensors may be used in various embodiments. The substrate 602 may include a non-conductive material, such as polyethylene naphthalate (PEN), polyimide, or any other suitable non-conductive material. In some embodiments, a thickness of the substrate may be selected to facilitate a secure connection to a type of zero insertion force (ZIF) connector (e.g., substrate thickness of 250 μm).

The sensors 604A-604D may include any suitable electrode material such as copper, graphite, titanium, silver, gold, platinum, or combinations thereof. The sensors 604A-604D may further be shaped to facilitate electrical contact with external components to provide improved output. A single counter electrode 606 may also be formed on the substrate 602, which may be shared by each of the sensors 604A-604D to reduce the total number of electrodes on the sensor chip 600. In some embodiments, multiple return electrodes such as common electrode 606 may also be used in a sensor.

The sensors 604A-604D and the common electrode 606 may together define a region with interdigitated electrodes 608. FIG. 6B illustrates a cross-section through the interdigitated electrodes 608 of the sensors 604A-604C, which shows an active region 610 defined between the interdigitated electrodes 608 where a gas-sensing material may be deposited. In certain embodiments, a thickness of the interdigitated electrodes 608 may range from 100 nm to 1 μm. A pitch 610 between adjacent interdigitated electrodes 608 may range, for example, from 50 μm to 5 mm.

The sensor chip 600 may be designed such that a portion of the sensor chip 600 can be directly inserted into an electrical connector for resistance measurement. In order to achieve desired resistance levels of the printed substance, the sensor chip 600 can be designed to vary the number, duty cycle, and dimensions (including thickness) of interdigitated electrodes 608, as well as the gap distance between adjacent electrodes. The dimensions of the printed leads of the sensors 604A-604D may be chosen such that the lead resistances for the common electrode path and the sensor path are nearly in order to cancel out their influence in the resistance measurements. The substrate 602 may be designed for ratiometric 3-wire resistance measurements, but may also be compatible with traditional 3-wire resistance measurements and 2-wire resistance measurements.

FIG. 6C illustrates the operation of the sensor chip 600, which is illustrated as being operatively coupled to a processing device 650 having a number of pins 654. The processing device may include one or more electronic components, such as a multiplexer 652, that may be configured to measure the resistivity of the gas sensing material using the various on-chip sensors. In some embodiments, the processing device 650 represents one or more general-purpose processing devices such as a microprocessor, central processing unit, or the like. For example, the processing device 650 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 650 may also be one or more special-purpose processing devices such as an application specific integrated circuit (ASIC), a field programmable gate array (FPGA), a digital signal processor (DSP), network processor, or the like. The processing device 650 may be configured to perform various operations, such as applying electrical signals, measuring electrical signals, and computing data based on the measured electrical signals. In certain embodiments, the processing device 650 may be a single device or a device that controls other devices. For example, the processing device 650 may be configured to perform resistivity measurements, or may control one or more other devices that perform resistivity measurements.

Figure 7:
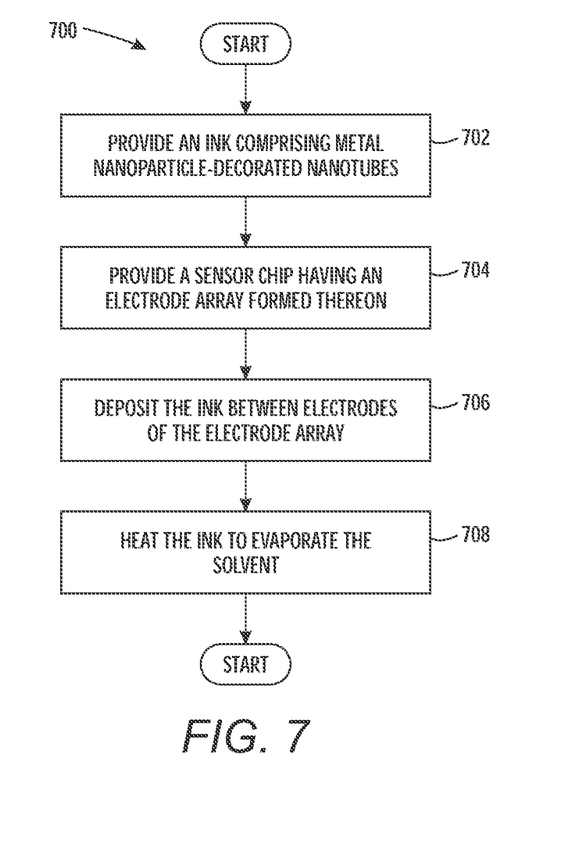
FIG. 7 is a flow diagram depicting an example method of fabricating a nanoparticle based sensor, according to some aspects of the disclosure.

FIG. 7 is a flow diagram illustrating a method 700 for fabricating a sensor in accordance with embodiments of the present disclosure. The method 700 begins at block 702, where an ink comprising metal nanoparticle-decorated nanotubes is provided. The metal nanoparticle-decorated nanotubes may correspond to any metal nanoparticle-decorated nanotubes described herein (e.g., PVP-coated palladium nanoparticles bound to SWCNTs).

At block 704, a sensor chip or substrate having an electrode array formed thereon is provided. For example, a substrate and sensor as described with reference to FIG. 6 may be provided. At block 706, the ink is deposited between electrodes of the electrode array, and the solvent of the ink is allowed to evaporate leaving a gas-sensing material comprising metal nanoparticle-decorated nanotubes. For example, an ink may be provided having metal nanoparticle decorated nanotubes as described above. In certain embodiments, the ink is deposited by printing directly (e.g., using inkjet printing) on the sensors. In some embodiments, the ink is deposited using other suitable methods, such as pipetting, spin-coating, or dip-coating.

At block 708, the sensor may be heated of about a temperature of about 100° C. to evaporate the solvent. In some embodiments, the sensor may be heated at a higher or lower temperature to evaporate the solvent.

In some embodiments, a sensor produced according to the method 700 may operate over a wide relative humidity range in ambient conditions. As used herein, "ambient conditions" refers to the conditions of a typical laboratory environment with a temperature of 20±5° C. and a pressure of 1±0.1 atmospheres (ATM). In certain embodiments, during operation of the sensor in an ambient environment having a relative humidity from 0% to 80%, the sensor has a methane detection limit of 100 ppm. In some embodiments, the sensor may have a lower detection limit, e.g., 50 ppm or 10 ppm. The sensor may achieve such performance over a temperature range outside of the ambient conditions (e.g., from −5° to 50° C.).

Printed methane sensors based on hydrophobic sensing particles suffer from reduced performance in high and prolonged humidity environment. Disclosed herein are structures and processes for fabrication of highly hydrophobic polymer-coated metal nanoparticle decorated CNTs with a final annealing step at >350 deg. C., in vacuum or inert gas. The method increases the contact between the SWCNT surface and the metal nanoparticles. This produces sensors with improved sensitivity and detection limits and with increased lifetime in humid conditions.

Various operations are described as multiple discrete operations, in turn, in a manner that is most helpful in understanding the present disclosure, however, the order of description may not be construed to imply that these operations are necessarily order dependent. In particular, these operations need not be performed in the order of presentation.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely exemplary. Particular embodiments may vary from these exemplary details and still be contemplated to be within the scope of the present disclosure.

Additionally, some embodiments may be practiced in distributed computing environments where the machine-readable medium is stored on and or executed by more than one computer system. In addition, the information transferred between computer systems may either be pulled or pushed across the communication medium connecting the computer systems.

Embodiments of the claimed subject matter include, but are not limited to, various operations described herein. These operations may be performed by hardware components, software, firmware, or a combination thereof.

Although the operations of the methods herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent or alternating manner.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such. Furthermore, the terms "first," "second," "third," "fourth," etc. as used herein are meant as labels to distinguish among different elements and may not necessarily have an ordinal meaning according to their numerical designation.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims. The claims may encompass embodiments in hardware, software, or a combination thereof.

What is claimed is:

1. A composition of matter comprising:
a first set of carbon nanotubes decorated with polymer-coated metal nanoparticles produced based on a mixture of a carbon nanotube dispersion and a polymer coated metal nanoparticle dispersion, wherein the polymer coating attaches the metal nanoparticles to the carbon nanotubes and reduces adsorption of water vapor by the metal nanoparticles;
a first amount of oxygenated functional groups achieved based on an annealing process with a temperature above 300 degrees Celsius, wherein the first amount is within twenty percent of a weight of the composition of matter; and
a first water contact angle achieved based on the annealing process, wherein the first water contact angle is higher than eighty two degrees.

2. The composition of matter of claim 1, wherein the metal nanoparticles comprise a metal selected from a group consisting of palladium, iridium, rhodium, platinum, copper, nickel, chromium, ruthenium, silver and gold.

3. The composition of matter of claim 2, wherein the metal nanoparticles are produced by using a mixture of two or more salts of two or more metal ion salts, wherein ions in the two or more metal ion salts are in a group comprising palladium, iridium, rhodium, platinum, copper, nickel, chromium, ruthenium, silver and gold ions.

4. The composition of matter of claim 1, wherein the carbon nanotubes comprise single-walled carbon nanotubes.

5. The composition of matter of claim 1, wherein the polymer coated metal nanoparticles comprises a polymer layer.

6. The composition of matter of claim 5, wherein the polymer layer comprises polyvinylpyrrolidone, and wherein the metal nanoparticles comprise palladium or platinum.

7. The composition of matter of claim 1, wherein the composition of matter is hydrophobic.

8. The composition of matter of claim 1, wherein the annealing process is performed at above 350° C.

9. The composition of matter of claim 1, wherein a residual polymer content of the composition of matter achieved based on the annealing process is less than 50%.

10. The composition of matter of claim 1, wherein the annealing process is performed in a vacuum or inert gas environment.

11. A sensor for detecting gas, the sensor comprising:
an electrode assembly comprising electrodes; and
a gas-adsorbing material disposed between the electrodes of the electrode assembly, wherein the sensor is associated with a detection limit achieved based on an annealing process with a temperature above 300 degrees Celsius; and
wherein the gas-adsorbing material comprises:
a first set of carbon nanotubes decorated with polymer-coated metal nanoparticles produced based on a mixture of a carbon nanotube dispersion and a polymer coated metal nanoparticle dispersion, wherein the polymer coating attaches the metal nanoparticles to the carbon nanotubes and reduces adsorption of water vapor by the metal nanoparticles;
a first amount of oxygenated functional groups achieved based on the annealing process, wherein the first amount is within twenty percent of a weight of the composition of matter; and
a first water contact angle achieved based on the annealing process, wherein the first water contact angle is higher than eighty two degrees.

12. The sensor of claim 11, wherein the metal nanoparticles comprise a metal selected from a group consisting of palladium, iridium, rhodium, platinum, copper, nickel, chromium, ruthenium, silver and gold.

13. The sensor of claim 12, wherein the metal nanoparticles are produced by using a mixture of two or more salts of two or more metal ion salts, wherein ions in the two or more metal ion salts are in a group comprising palladium, iridium, rhodium, platinum, copper, nickel, chromium, ruthenium, silver and gold ions.

14. The sensor of claim 11, wherein the carbon nanotubes comprise single-walled carbon nanotubes.

15. The sensor of claim 11, wherein the polymer coated metal nanoparticles comprises a polymer layer.

16. The sensor of claim 15, wherein the polymer layer comprises polyvinylpyrrolidone, and wherein the metal nanoparticles comprise palladium or platinum.

17. The sensor of claim 11, wherein the composition of matter is hydrophobic.

18. The sensor of claim 11, wherein the annealing process is performed at above 350° C.

19. The sensor of claim 11, wherein a residual polymer content of the composition of matter achieved based on the annealing process is less than 50%.

20. The sensor of claim 11, wherein the annealing process is performed in a vacuum or inert gas environment.

* * * * *